US010039186B2

(12) United States Patent
Baxi et al.

(10) Patent No.: US 10,039,186 B2
(45) Date of Patent: Jul. 31, 2018

(54) STRETCHABLE AND FLEXIBLE ELECTRICAL SUBSTRATE INTERCONNECTIONS

(71) Applicant: Intel Corporation, Santa Clara, CA (US)

(72) Inventors: Amit Sudhir Baxi, Bangalore (IN); Vincent S. Mageshkumar, Navi Mumbai (IN); Adel A. Elsherbini, Chandler, AZ (US); Sasha Oster, Chandler, AZ (US); Feras Eid, Chandler, AZ (US); Aleksandar Aleksov, Chandler, AZ (US); Johanna M. Swan, Scottsdale, AZ (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 15/267,872

(22) Filed: Sep. 16, 2016

(65) Prior Publication Data

US 2018/0084643 A1 Mar. 22, 2018

(51) Int. Cl.
*H05K 1/00* (2006.01)
*H05K 1/14* (2006.01)
(Continued)

(52) U.S. Cl.
CPC ........... *H05K 1/147* (2013.01); *H05K 1/0283* (2013.01); *H05K 1/112* (2013.01); *H05K 1/181* (2013.01);
(Continued)

(58) Field of Classification Search
CPC .... H05K 1/0277; H05K 1/0283; H05K 1/147; H01R 13/62; H01R 12/71; H01R 12/77; H01R 13/627
(Continued)

(56) References Cited

U.S. PATENT DOCUMENTS 4,067,342 A 1/1978 Burton
4,259,965 A 4/1981 Fukuda et al.
(Continued)

FOREIGN PATENT DOCUMENTS

JP 06333648 A 12/1994
WO WO-03065926 A2 8/2003
(Continued)

OTHER PUBLICATIONS

US 9,865,941, 01/2018, Oster (withdrawn)
(Continued)

*Primary Examiner* — Steven T Sawyer
(74) *Attorney, Agent, or Firm* — Schwegman Lundberg & Woessner, P.A.

(57) ABSTRACT

A circuit interconnect may be used in biometric data sensing and feedback applications. A circuit interconnect may be used in device device-to-device connections (e.g., Internet of Things (IoT) devices), including applications that require connection between stretchable and rigid substrates. A circuit interconnect may include a multi-pin, snap-fit attachment mechanism, where the attachment mechanism provides an electrical interconnection between a rigid substrate and a flexible or stretchable substrate. The combination of a circuit interconnect and flexible or stretchable substrate provides improved electrical connection reliability, allows for greater stretchability and flexibility of the circuit traces, and allows for more options in connecting a stretchable circuit trace to a rigid PCB.

19 Claims, 8 Drawing Sheets

(51) Int. Cl.
*H05K 1/18* (2006.01)
*H05K 1/02* (2006.01)
*H05K 1/11* (2006.01)

(52) U.S. Cl.
CPC .............. *H05K 2201/10151* (2013.01); *H05K 2201/10265* (2013.01); *H05K 2201/10303* (2013.01)

(58) Field of Classification Search
USPC .................................................. 439/37, 638
See application file for complete search history.

(56) References Cited

U.S. PATENT DOCUMENTS

| | | | |
|---|---|---|---|
| 5,499,927 | A | 3/1996 | Ohno et al. |
| 5,507,303 | A | 4/1996 | Kuzma |
| 6,096,066 | A | 8/2000 | Chen et al. |
| 6,496,705 | B1 | 12/2002 | Ng et al. |
| 6,697,262 | B2 | 2/2004 | Adams et al. |
| 7,524,195 | B2 | 4/2009 | Ales et al. |
| 7,637,747 | B2 | 12/2009 | Jaatinen et al. |
| 9,391,394 | B2 | 7/2016 | Kockx et al. |
| 9,735,893 | B1 | 8/2017 | Aleksov et al. |
| 9,893,438 | B1 | 2/2018 | Elsherbini et al. |
| 2006/0124193 | A1* | 6/2006 | Orr .................. A61B 5/0002 139/421 |
| 2006/0197213 | A1 | 9/2006 | Lian |
| 2006/0224067 | A1 | 10/2006 | Giftakis et al. |
| 2006/0246744 | A1 | 11/2006 | Marmaropoulos et al. |
| 2006/0252284 | A1 | 11/2006 | Marmaropoulos et al. |
| 2007/0100219 | A1 | 5/2007 | Sweitzer et al. |
| 2007/0129776 | A1 | 6/2007 | Robins et al. |
| 2007/0184682 | A1* | 8/2007 | Gobron .............. A61B 5/04085 439/67 |
| 2008/0004515 | A1 | 1/2008 | Jennewine |
| 2009/0054737 | A1 | 2/2009 | Magar et al. |
| 2009/0076363 | A1 | 3/2009 | Bly et al. |
| 2009/0076559 | A1 | 3/2009 | Libbus et al. |
| 2009/0131838 | A1 | 5/2009 | Fotiadis et al. |
| 2009/0149037 | A1 | 6/2009 | Lee et al. |
| 2009/0182393 | A1 | 7/2009 | Bachinski |
| 2009/0203244 | A1 | 8/2009 | Den Toonder et al. |
| 2009/0306485 | A1 | 12/2009 | Bell et al. |
| 2010/0125190 | A1 | 5/2010 | Fadem |
| 2010/0136804 | A1 | 6/2010 | Strickland |
| 2010/0304530 | A1 | 12/2010 | Yim et al. |
| 2012/0157807 | A1 | 6/2012 | Virtanen et al. |
| 2012/0238890 | A1 | 9/2012 | Baker et al. |
| 2012/0295451 | A1 | 11/2012 | Hyun-jun et al. |
| 2013/0030259 | A1 | 1/2013 | Thomsen et al. |
| 2013/0065406 | A1 | 3/2013 | Rohrbach et al. |
| 2013/0109937 | A1 | 5/2013 | Banet et al. |
| 2013/0111710 | A1 | 5/2013 | Hunts |
| 2013/0160183 | A1* | 6/2013 | Reho .................. A41D 13/1281 2/69 |
| 2013/0166006 | A1 | 6/2013 | Williams |
| 2013/0273752 | A1 | 10/2013 | Rudisill et al. |
| 2013/0338746 | A1* | 12/2013 | Guvanasen .......... A61N 1/0502 607/116 |
| 2014/0162468 | A1 | 6/2014 | Kim |
| 2014/0256193 | A1* | 9/2014 | Williams ............. H01R 12/716 439/696 |
| 2014/0335714 | A1 | 11/2014 | Schrader |
| 2015/0087949 | A1 | 3/2015 | Felix et al. |
| 2015/0150502 | A1 | 6/2015 | Wu |
| 2015/0303619 | A1 | 10/2015 | Kockx et al. |
| 2016/0045135 | A1 | 2/2016 | Kim et al. |
| 2016/0099517 | A1 | 4/2016 | Fernandes et al. |
| 2016/0121098 | A1 | 5/2016 | Kockx et al. |
| 2016/0157779 | A1 | 6/2016 | Baxi et al. |
| 2016/0172320 | A1 | 6/2016 | Swaminathan et al. |
| 2016/0181729 | A1 | 6/2016 | Barth et al. |
| 2016/0296159 | A1 | 10/2016 | Larson et al. |
| 2018/0020982 | A1 | 1/2018 | Elsherbini et al. |
| 2018/0026393 | A1 | 1/2018 | Eid et al. |
| 2018/0026730 | A1 | 1/2018 | Aleksov et al. |

FOREIGN PATENT DOCUMENTS

| | | |
|---|---|---|
| WO | WO-2009036327 A1 | 3/2009 |
| WO | WO-2016010983 A1 | 1/2016 |
| WO | WO-2018017205 A1 | 1/2018 |
| WO | WO-2018017206 A1 | 1/2018 |

OTHER PUBLICATIONS

"U.S. Appl. No. 15/216,502, Examiner Interview Summary dated Feb. 1, 2017", 3 pgs.
"U.S. Appl. No. 15/216,502, Non Final Office Action dated Dec. 15, 2016", 15 pgs.
"U.S. Appl. No. 15/216,502, Notice of Allowance dated Apr. 5, 2017", 5 pgs.
"U.S. Appl. No. 15/216,502, Response filed Feb. 17, 2017 to Non Final Office Action dated Dec. 15, 2016", 11 pgs.
"U.S. Appl. No. 15/281,814, Non Final Office Action dated Apr. 10, 2017", 10 pgs.
"International Application Serial No. PCT/US2016/040476, International Search Report dated Jan. 10, 2107", 4 pgs.
"International Application Serial No. PCT/US2016/040476, Written Opinion dated Jan. 10, 2017", 8 pgs.
"Listen to Your Heart Arrythmias", iRhythm Technologies, [Online]. Retrieved from the Internet: <URL: http://www.irhythmtech.com/patients-heart-arrhythmias-afib.php, (Accessed Mar. 31, 2016), 5 pgs.
"SEEQ™ Mobile Cardiac Telemetry (MCT) Device", [Online]. Retrieved from the Internet: <URL: http//www.medtronicdiagnostics.com/us/cardiac-monitors/seeq-mct-system/seeq-mct-device/index.htm, (Accessed Mar. 31, 2016), 4 pgs.
"U.S. Appl. No. 15/215,531, Final Office Action dated Sep. 22, 2017", 13 pgs.
"U.S. Appl. No. 15/215,531, Non Final Office Action dated May 15, 2017", 13 pgs.
"U.S. Appl. No. 15/215,531, Notice of Allowability dated Jan. 12, 2018", 2 pgs.
"U.S. Appl. No. 15/215,531, Notice of Allowance dated Dec. 15, 2017", 7 pgs.
"U.S. Appl. No. 15/215,531, Response filed Jul. 20, 2017 to Non Final Office Action dated May 15, 2017", 17 pgs.
"U.S. Appl. No. 15/215,531, Response filed Nov. 14, 2017 to Final Office Action dated Sep. 22, 2017", 12 pgs.
"U.S. Appl. No. 15/281,814, Corrected Notice of Allowance dated Jan. 16, 2018", 2 pgs.
"U.S. Appl. No. 15/281,814, Notice of Allowance dated Sep. 6, 2017", 7 pgs.
"U.S. Appl. No. 15/281,814, Response to Non Final Office Action dated Apr. 10, 2017", 5 pgs.
"U.S. Appl. No. 15/676,611, Examiner Interview Summary dated Nov. 8, 2017", 3 pgs.
"U.S. Appl. No. 15/676,611, Non Final Office Action dated Sep. 5, 2017", 6 pgs.
"U.S. Appl. No. 15/676,611, Notice of Allowance dated Nov. 20, 2017", 5 pgs.
"U.S. Appl. No. 15/676,611, Response Filed Nov. 6, 2107 to Non Final Office Action dated Sep. 5, 2017", 8 pgs.
"International Application No. PCT/US2017/037298, International Search Report dated Aug. 14, 2017", 4 pgs.
"International Application No. PCT/US2017/037298, Written Opinion dated Aug. 14, 2017", 7 pgs.
"International Application No. PCT/US2017/037301, International Search Report dated Sep. 8, 2017", 3 pgs.
"International Application No. PCT/US2017/037301, Written Opinion dated Sep. 8, 2017", 8 pgs.
"International Application No. PCT/US2017/046014, International Search Report dated Nov. 17, 2017", 4 pgs.
"International Application Serial No. PCT/US2017/046014, Written Opinion dated Nov. 17, 2017", 7 pgs.

(56) References Cited

OTHER PUBLICATIONS

"International Application Serial No. PCT/US2017/049159, International Search Report dated Dec. 11, 2017", 3 pgs.
"International Application Serial No. PCT/US2017/049159, Written Opinion dated Dec. 11, 2017", 7 pgs.
Andrew, A. Kostrzewski, et al., "Innovative, wearable snap connector technology for improved networking in electronic garments", (May 2, 2007), 8 pgs.
"U.S. Appl. No. 15/215,529, Non Final Office Action dated Apr. 19, 2018", 11 pgs.

* cited by examiner

STRETCHABLE AND FLEXIBLE ELECTRICAL SUBSTRATE INTERCONNECTIONS

TECHNICAL FIELD

Embodiments described herein generally relate to electrical interconnections in wearable electronic devices.

BACKGROUND

Wearable electronic devices may be used to provide personal, mobile biometric data collection and biometric feedback. These wearable devices may be used for fitness applications, wellness applications, or healthcare management applications. Existing wearable technologies include rigid circuit boards within rigid housings such as clip-on pedometers, or include rigid circuit boards within flexible housings such as wristwatch devices. It is desirable to improve the flexibility of wearable electronic devices while reducing the difficulties associated with flexible electronic devices.

DESCRIPTION OF EMBODIMENTS

Figure 1:
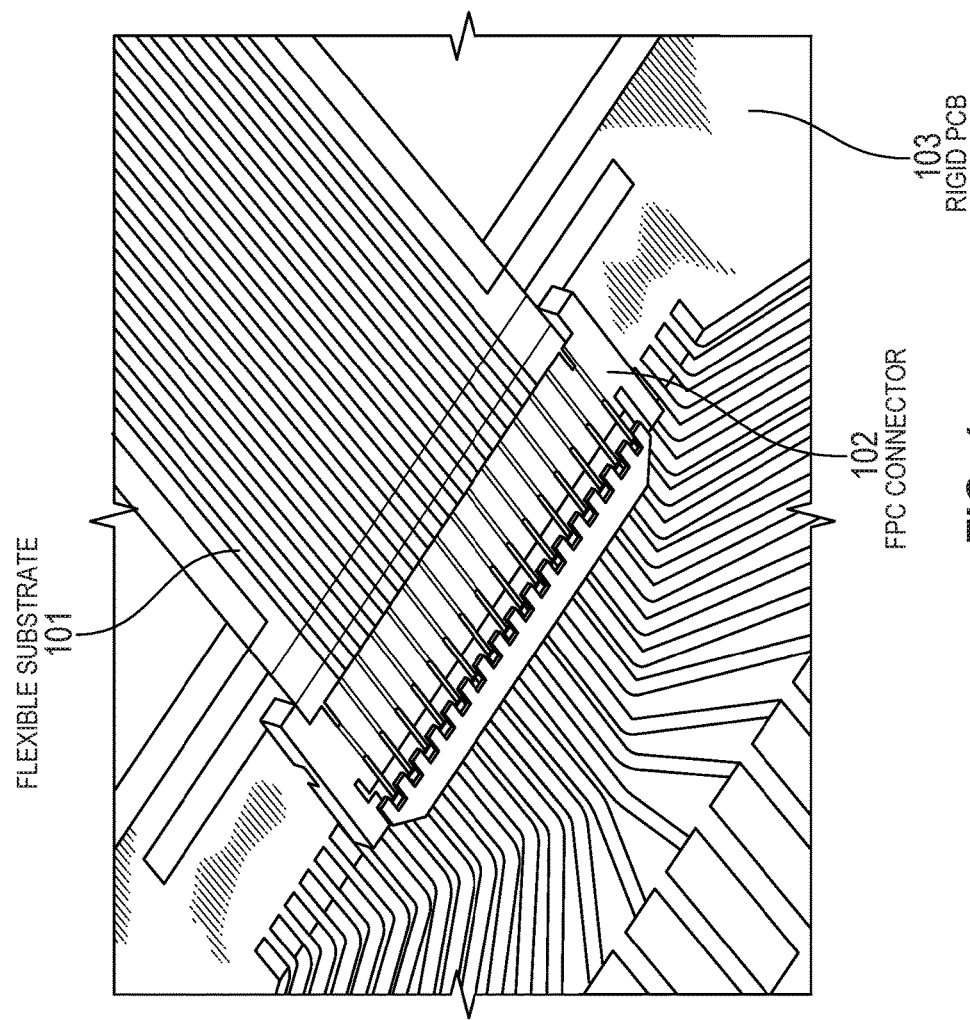
FIG. 1 is a perspective diagram of a flexible printed circuit (FPC) assembly, in accordance with at least one embodiment of the invention.

The present subject matter includes a circuit interconnect for use in biometric data sensing and feedback applications. In various embodiments, the circuit interconnect may be used to electrically interconnect two or more circuit substrates that are rigid, flexible, stretchable, or various combinations of rigid, flexible, or stretchable. In an example, the circuit interconnect includes a multi-pin, snap-fit attachment mechanism, where the attachment mechanism provides an electrical interconnection between a rigid substrate and a flexible or stretchable substrate.

Stretchable circuit board technology addresses technical problems facing flexible and rigid circuit boards. A technical problem faced by flexible circuit boards includes an unreliability of the circuit traces within the flexible circuit board. For example, repeated flexion of the circuit traces may result in additional noise on the circuit traces, delamination of flexible circuit board layers, and eventually breaking of the circuit traces. Flexible circuit boards are also designed to flex in a particular direction, limiting the range of motion. Additionally, flexible circuit boards are generally designed to interface with a rigid PCB at a single connection point on a side of the rigid PCB, which further limits range of motion and places additional design constraints on the flexible and rigid PCB devices.

Stretchable circuit board interconnect technology provides technical solutions to the technical problems facing flexible and rigid circuit boards. The stretchable circuit interconnect provides improved electrical connection reliability, allows for greater stretchability and flexibility of the circuit traces, and allows for more options in connecting a stretchable circuit trace to a rigid PCB.

Improved flexible and stretchable electrical connections can be used to create flexible wearable devices and flexible wearable devices. Flexible and stretchable electronics may also be used to create disposable electronic devices or disposable sensor portions of wearable electronic devices. As wearable electronic devices increasingly incorporate disposable parts, it becomes increasingly important to have an easy to use, reliable, and low-cost attachment of flexible disposable electronic parts to rigid and non-disposable electronic sub-systems (e.g. for attachment to wireless sensor nodes). The circuit interconnect may be used within a wearable biometric data sensing device, such as a wearable sensor that provides data to an associated smartphone, personal computer (PC), or other electronic device. The circuit interconnect may be used within a standalone electronic device, such a wristband or headband. The circuit interconnect may be used within a standalone sensor device that can be connected with an external electronic device, where the standalone sensor device may include a shirt, a sock, a sweatband, or other apparel. These devices may be used for personal biometric monitoring, remote biometric monitoring, or for use in device-to-device connections (e.g., Internet of Things (IoT) devices). The circuit interconnect may be used in combination with various types of interconnects, including specially designed interconnects such as the Common System Interface (CSI), the QuickPath Interconnect (QPI), Ultra Path Interconnect (UPI), or Keizer Technology Interconnect (KTI).

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

FIG. 1 is a perspective diagram of a flexible printed circuit (FPC) assembly 100, in accordance with at least one embodiment of the invention. FPC assembly 100 includes a flexible printed circuit (FPC) 101, an FPC connector 102, and a rigid printed circuit board (PCB) 103. The FPC connector 102 may mounted on the rigid PCB 103 during manufacturing. One end of the FPC 101 is inserted into the FPC connector 102, and secured in the FPC connector using a friction fit, a clamp, leaf spring metallic contacts, or another connector retention mechanism within FPC connector 102. The FPC connector 102 is placed at the edge of the rigid PCB 103, which requires electrical connections to be concentrated in the location of the FPC connector 102 and brought out at the edge of the rigid PCB 103. This edge connection results in some constraints on the industrial design or form-factor of wearable devices. When the FPC 101 is inserted into the FPC connector 102, the contacts within the FPC connector 102 generate a weak, friction-induced pressure on the substrate of the FPC 101. This relatively weak electromechanical connection may result in additional noise introduced into the signals within the FPC assembly 100. Significant additional noise may be introduced into the FPC assembly 100 when the FPC assembly 100 is implemented in a wearable device, especially when the wearable system is subjected to motion due to physical activity of the user. An improved FPC system is shown and described with respect to FIGS. 2A-2B.

Figure 2A:
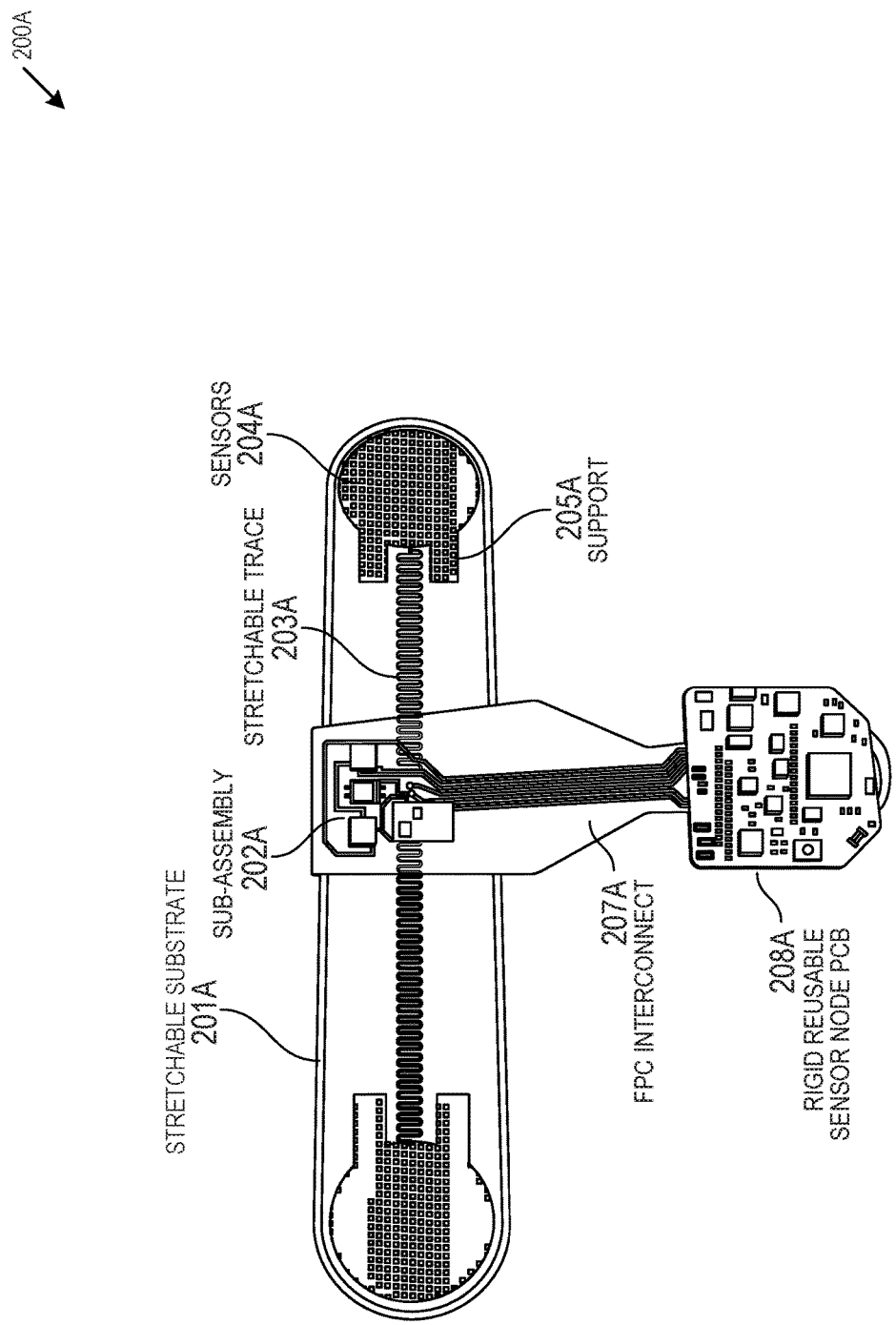
FIGS. 2A-2B are perspective diagrams of a first and second stretchable circuit assembly, in accordance with at least one embodiment of the invention.
Figure 2B:
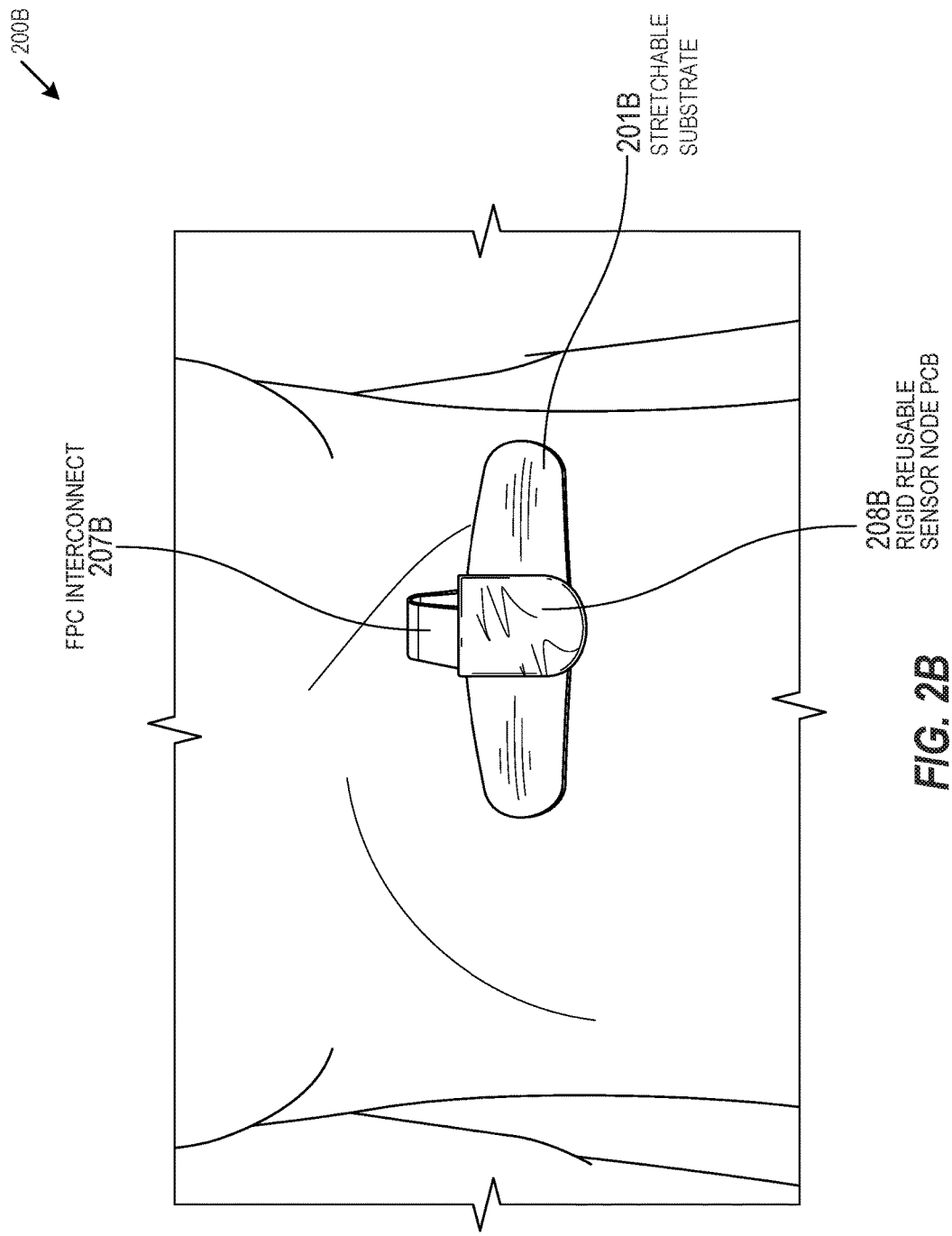

FIGS. 2A-2B are perspective diagrams of a first and second stretchable circuit assemblies 200A-200B, in accordance with at least one embodiment of the invention. First assembly 200A depicts wearable system that uses an FPC connector to connect flex and rigid substrates. First assembly 200A includes a stretchable substrate 201A connected to a sub-assembly 202A. The stretchable substrate includes one or more stretchable traces 203A and one or more substrate-mounted sensors 204A. The substrate-mounted sensors 204A are configured to contact the skin of a user, and may be used to collect biometric data. The substrate-mounted sensors 204A may include one or more support extensions 205A, where the support extensions 205A may overlap at least a portion of the stretchable trace 203A. The support extensions 205A improve contact between the stretchable trace 203A and the sensors 204A by providing structural support and reducing stretching in that area. The stretchable traces 203A or substrate-mounted sensors 204A can detect various physical configurations or activities based on electrical characteristics. In an example, a torsion or extension of the stretchable trace 203A or sensors 204A may change a measured capacitance, resistance, or another electrical characteristic, which may be sensed by the sub-assembly 202A. The sub-assembly 202A is mounted on an FPC interconnect 207A. The FPC interconnect 207A provides a flexible connection between the stretchable substrate 201A and a rigid PCB 208A. Rigid PCB 208A may include a sensor node, a microcontroller, a processor, a wireless radio, or other circuitry. Rigid PCB may be folded over and attached to the sub-assembly 202A, such as shown in FIG. 2B.

Second assembly 200B depicts wearable system that uses an FPC connector to connect flex and rigid substrates. Second assembly 200B is depicted as a strip that is adhered to a user's chest, where second assembly 200B may be used to monitor biometric data continuously. Second assembly 200B includes a stretchable substrate 201B, where the stretchability of substrate 201B enables second assembly 200B to adhere to the chest and monitor biometric data during periods of sedentary activity, vigorous activity, and other activity levels. An FPC interconnect 207B provides a flexible connection between the stretchable substrate 201B and a rigid PCB 208B. The stretchable substrate 201B may be disposable, and may be combined with a reusable (e.g., non-disposable) rigid PCB 208B. For example, the stretchable substrate 201B may be replaced when an older stretchable substrate does not provide the desired stretchability, adhesion, biometric signal detection, or signal transmission.

The stretchable circuit assemblies 200A-200B provide solutions to technical problems facing FPCs. For example, each FPC is connected to a rigid PCB through a connector, which requires that all signals be brought out from the rigid PCB to the FPC in the form of a bus or cable. Often, this connection is formed only at the edge of a flexible substrate. The FPC connection and the limited flexibility of the FPC imposes electrical and mechanical constraints on the form-factor and design of the wearable FPC device. For example, in a wearable biometric sensing system, it is desirable to minimize the forces induced by user movement on the biometric sensors that contact the skin. One way to reduce the strain is to create a patch form-factor design such that relatively heavier electronic components are at the center of the module, where the module is attached firmly to the user's body to minimize forces induced by user movement. FIGS. 2A-2B show one technical solution, which includes fixing the relatively heavier rigid PCB 208B to the center of the stretchable substrate 201B. This configuration secures the most massive components in the center of the stretchable circuit assemblies 200A-200B, which reduces forces induced by user movement.

Figure 3:
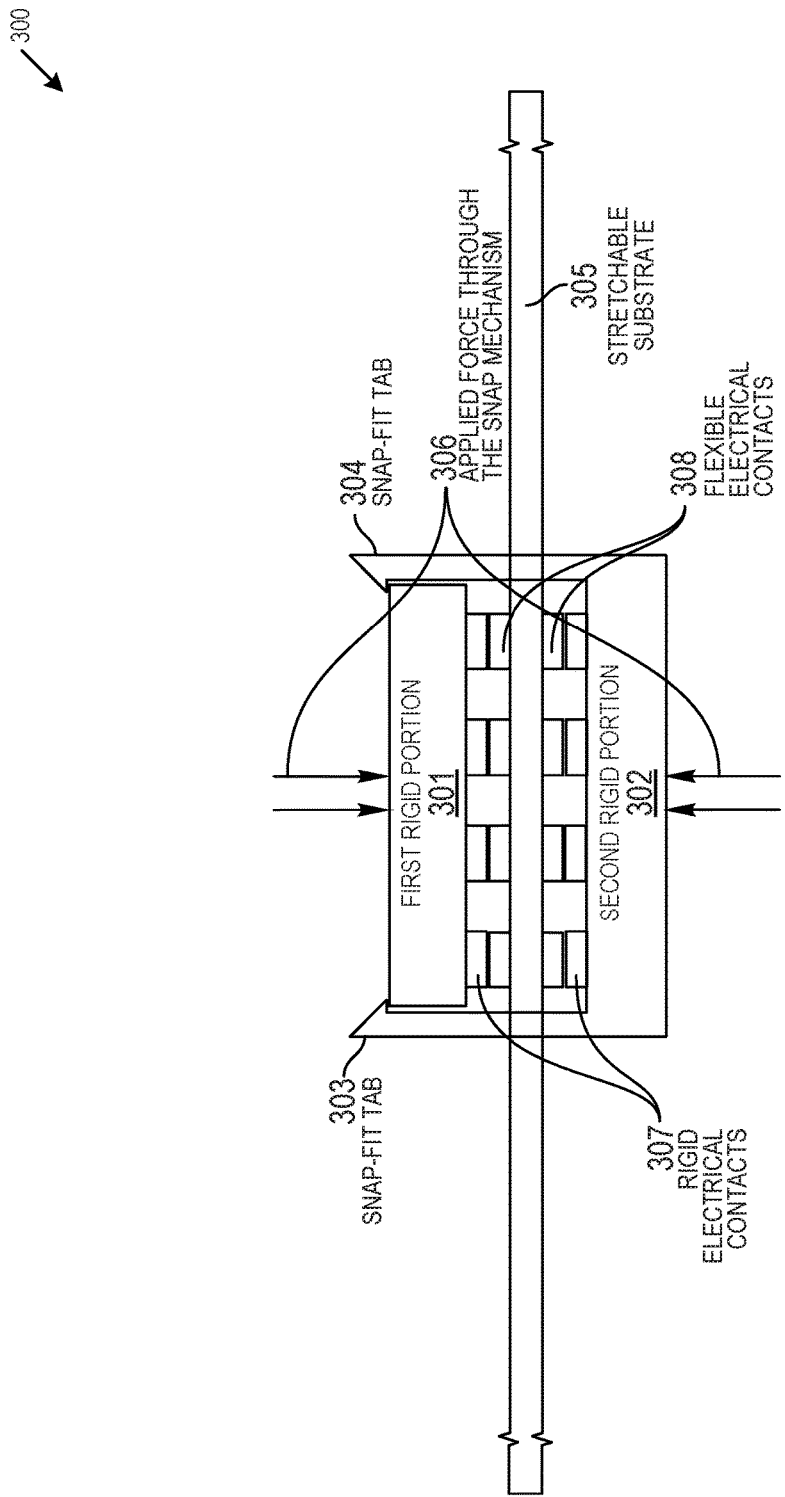
FIG. 3 is a block diagram of a third stretchable circuit assembly, in accordance with at least one embodiment of the invention.

FIG. 3 is a block diagram of a third stretchable circuit assembly 300, in accordance with at least one embodiment of the invention. Stretchable circuit assembly 300 includes a first rigid portion 301 and a second rigid portion 302. The second rigid portion 302 includes a snap-fit mechanism, such as snap fit tab 304 and snap fit tab 305. A stretchable substrate 305 is disposed between the first rigid portion 301 and the second rigid portion 302. The snap-fit mechanism applies a force 306 to the first rigid portion 301 and to the second rigid portion 302. The force 306 connects one or more rigid electrical contacts 307 with one or more flexible electrical contacts. Various combinations of rigid portions and contact sizes and shapes may be used, such as shown in FIG. 4.

Figure 4:
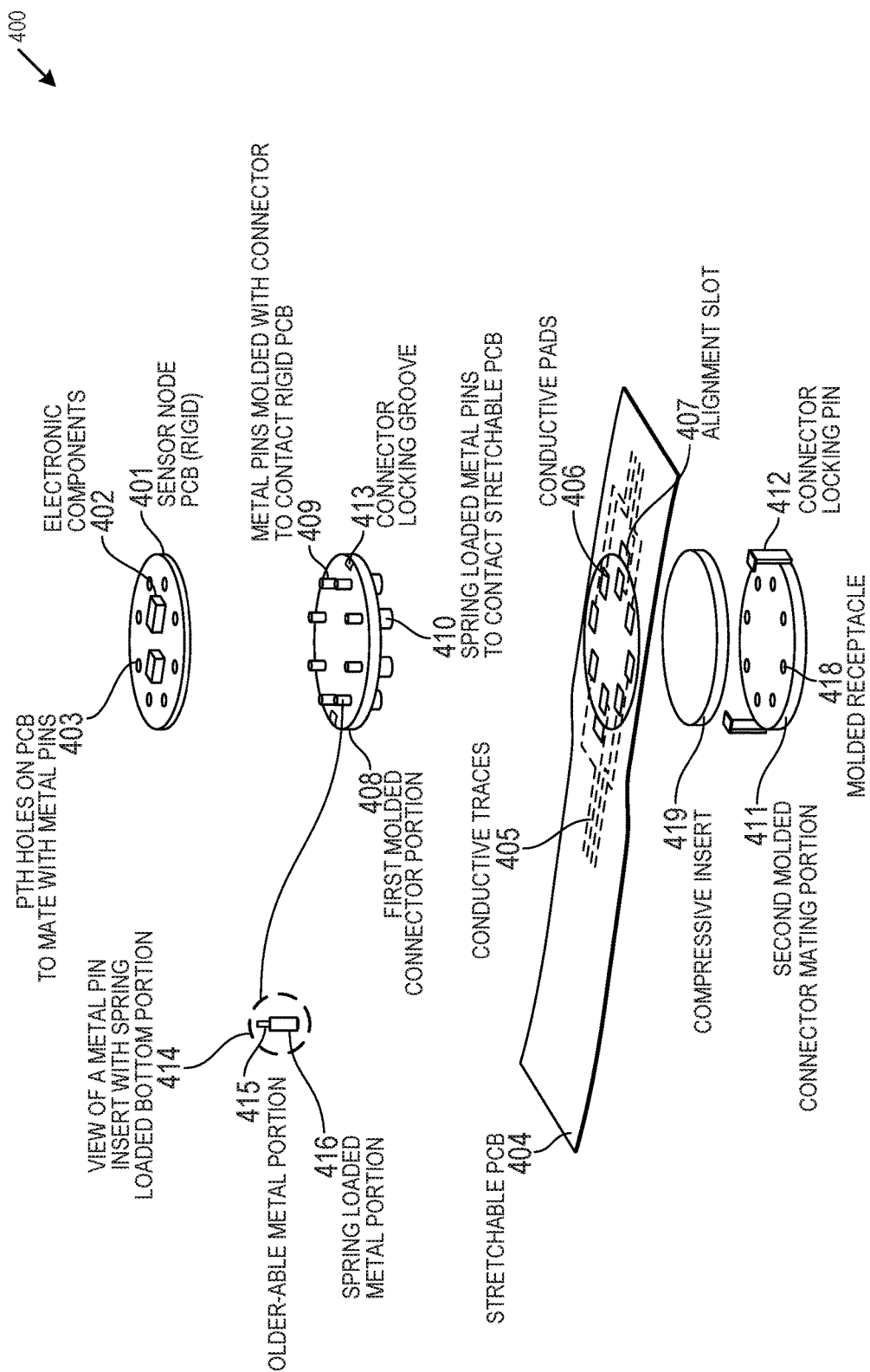
FIG. 4 is a perspective diagram of a fourth stretchable circuit assembly, in accordance with at least one embodiment of the invention.

FIG. 4 is a perspective diagram of a fourth stretchable circuit assembly 400, in accordance with at least one embodiment of the invention. Assembly 400 includes a stretchable PCB 404, where stretchable PCB 404 includes conductive traces 405 and conductive pads 406 fabricated on a flexible or stretchable substrate, such as polyamide polyimide, elastomer material, Thermoplastic Urethane (TPU), fabric, silicone, rubber, or other flexible or stretchable substrate. Assembly 400 includes a rigid sensor node PCB 401, where rigid PCB 401 includes plated-through-hole (PTH) mounting holes 403. In various embodiments, the rigid PCB 401 includes a cross-section that is circular, elliptical, rectangular, trapezoidal, or another cross-section shape. Rigid PCB 401 may be formed using rigid PCB technology, or may be formed using flexible PCB technology that is embedded in a rigid enclosure. The shape and structure of rigid PCB 401 may be selected based on the desired application. For example, a flexible PCB within a curved rigid structure may more comfortably match the curvature of the body in the area where the sensor node is to be placed, such as on an arm or on a knee.

Assembly 400 includes a first molded connector portion 408 and a second molded connector portion 411. The first molded connector portion 408 and second molded connector portion 411 may be manufactured using plastic injection molding, 3D printing, or other manufacturing technique. In various embodiments, the molded connector portions include cross-sections that are circular, elliptical, rectangular, trapezoidal, or other cross-section shapes. First molded connector portion 408 includes multiple pins molded within the plastic base. An example pin is shown as example pin 414. Example pin 414 includes a solderable metal portion 415, which are used to mate with PTH mounting holes 403. Example pin 414 also includes a spring-loaded metal portion 416, which is used to connect to the conductive pads 406 on the stretchable PCB 404. Example pin 414 may include other contacts, such as spring contacts or pins, such as POGO pins.

To provide electrical contacts, the rigid sensor node PCB 401 is placed on metal pins 409 so that the solderable portions of the pins pass through the PTH holes 403. The metal pins 409 are then soldered to the PTH holes 403 to create a single assembly. The spring-loaded metal pins 410 make contact with corresponding conductive pads 406 on the stretchable PCB 404. To provide proper alignment of spring-loaded metal pins 410 with corresponding conductive pads 406, the stretchable PCB 404 includes one or more alignment slots 407. Once properly aligned, one or more connector locking pins 412 pass through the alignment slots 407 and snap-fit with one or more connector locking grooves 413 on first molded connector portion 408. The connector locking pins 412 presses the stretchable PCB 404 from the underside, which presses the conductive pads 406 against the spring-loaded metallic contacts 410. The connector locking pins 412 also provide a simplified attachment and separation of components within the stretchable circuit assembly 400. For example, for implementations that include a stretchable PCB 404 that is disposable, the snap-fit configuration provided by the connector locking pins 412 simplifies the removal and replacement of the stretchable PCB 404.

Second molded connector portion 411 may also include one or more molded receptacles 418, where the molded receptacles 418 provide additional alignment and provide improved contact between the conductive pads 406 and the spring-loaded metallic contacts 410. Molded receptacles 418 may include additional structures to provide pressure, such as spring-loaded conical receptacle structures, conical receptacle pogo pins, or other spring-like structures. A compressive insert 419 may be included to provide additional pressure between the molded second molded connector portion 411 and the stretchable PCB 404. The compressive insert 419 may provide a uniform application of pressure, such as by acting like a common spring. A desired force may be determined for the stretchable circuit assembly 400, and the determined force may be provided by selecting a particular combination of forces provided by the locking pins 412, molded receptacles 418, compressive inserts 419, or additional spring-like structures. The desired force may be selected to reduce stretching in the area surrounding the metallic contacts 410, which further improves the mechanical and electrical contact between the spring-loaded metallic contacts 410 and the conductive pads 406.

The stretchable circuit assembly 400 provides various solutions to technical problems facing FPCs. A technical problem faced by wearable FPC devices is unreliable (e.g., weak) electrical connections. As described above, when a wearable FPC device is in motion, the unreliable electrical connections introduce noise into the system. The force provided within the stretchable circuit assembly 400 improves the contact quality and contact surface area between electrical connections, which improves the reliability of electromechanical connections even under intense movements. In particular, the force provided in the stretchable circuit assembly 400 significantly reduces motion related noise artifacts in biometric signals during vigorous or intense user movement.

Another technical problem faced by wearable FPC devices is the design constraints and inertial forces imposed by the limited flexibility of the FPC. As described above, in a wearable FPC device, it is desirable to minimize the forces induced by user movement on the biometric sensors that contact the skin. One solution is shown in FIGS. 2A-2B, which show a configuration that retains the rigid PCB 208B near the center of the stretchable substrate 201B. However, the FPC interconnect 207B is brought out in the form of a bus to connect with an FPC connector on the rigid PCB 208B, and the FPC and FPC connector cause the rigid PCB 208B to be offset from the exact center of the stretchable substrate 201B. The offset position of the rigid PCB 208B imposes additional inertial forces on the sensors that degrade biometric signal quality, especially during user movement. The structure provided within the stretchable circuit assembly 400 improves the center of gravity of the stretchable circuit assembly 400. Unlike a bus used in an FPC, the conductive pads 406 are dispersed along the surface of the stretchable PCB 404. This structure reduces design restrictions on the form-factor of the wearable device. Additionally, the distribution of the conductive pads 406, rigid sensor PCB 401, and other components may be selected to provide a desired center of gravity, such as by providing a wide surface area and a low z-height. This improved center of gravity provides improved signal quality by reducing the various inertial forces applied to different areas of the stretchable circuit assembly 400.

Yet another technical problem faced by wearable FPC devices is sealing the FPC connector against liquid and vapor ingress. As a result, the FPC contacts within wearable FPC devices are susceptible to humidity, rain, sweat, and other vapor or liquid. Because the FPC connector is required to connect the rigid PCB to the FPC, it is impractical to apply a vapor or liquid sealant to the FPC connector. The rounded structure provided within the stretchable circuit assembly 400 facilitates the sealing (e.g., potting) of the first molded portion 408 to the rigid sensor PCB 401. The compression and sealing reduces or prevents liquid and vapor ingress. Liquid ingress may be further reduced or prevented by means of compressive inserts 419 disposed on either side of the stretchable PCB 404. These compressive inserts 419 may be designed or selected to provide watertight seal when connector locking pins 412 pass through the alignment slots 407 and snap-fit with one or more connector locking grooves 413 on first molded connector portion 408. Compressive inserts 419 may be formed from silicone or rubber, or other compressive and hydrophobic (e.g., water-repellant) material. Additionally, the distribution of the conductive pads 406 and additional sealant between layers may be selected to isolate the contacts in case of liquid ingress.

Figure 5:
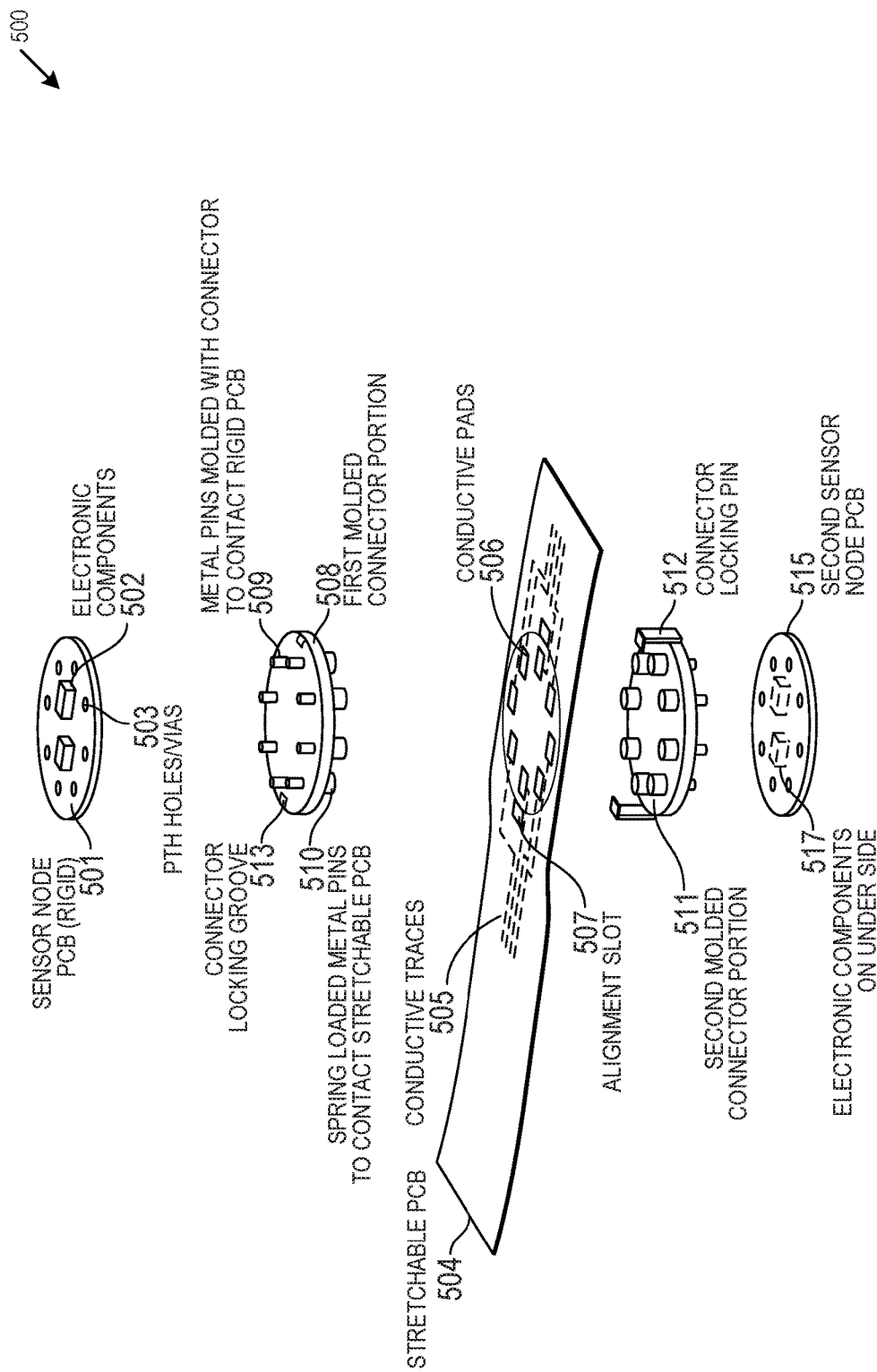
FIG. 5 is a perspective diagram of a fifth stretchable circuit assembly, in accordance with at least one embodiment of the invention.

FIG. 5 is a perspective diagram of a fifth stretchable circuit assembly 500, in accordance with at least one embodiment of the invention. Assembly 500 includes a stretchable PCB 504, where stretchable PCB 504 includes conductive traces 505 and conductive pads 506 fabricated on a flexible or stretchable substrate, such as polyamide polyimide, elastomer material, Thermoplastic Urethane (TPU), fabric, silicone, rubber, or other flexible or stretchable substrate. Assembly 500 includes a rigid sensor node PCB 501, where rigid PCB 501 includes plated-through-hole (PTH) mounting holes 503. Assembly 500 includes a first molded connector portion 508 and a second molded connector portion 511. The first molded connector portion 508 and second molded connector portion 511 may be manufactured using plastic injection molding, 3D printing, or other manufacturing technique. First molded connector portion 508 includes multiple pins molded within the plastic base. To provide electrical contacts, the rigid sensor node PCB 501 is placed on metal pins 509 so that the solderable portions of the pins pass through the PTH holes 503. The metal pins 509 are then soldered to the PTH holes 503 to create a single assembly. The spring-loaded metal pins 510 make contact with corresponding conductive pads 506 on the stretchable PCB 504. To provide proper alignment of spring-loaded metal pins 510 with corresponding conductive pads 506, the stretchable PCB 504 includes one or more alignment slots 507. Once properly aligned, one or more connector locking pins 512 pass through the alignment slots 507 and snap-fit with one or more connector locking grooves 513 on first molded connector portion 508.

In addition to some features in common with the fourth stretchable circuit assembly 400, the fifth stretchable circuit assembly 500 includes upper and lower portions that both include metal contacts and electronic components. Assembly 500 includes a disc-shaped second rigid PCB 515, where second rigid PCB 515 connects to one or more pins on the second molded connector portion 511. The stretchable PCB 504 further includes conductive contact pads 506 on the lower surface to contact pins on the second connector portion 511. The second rigid PCB 515 provides contacts and surface area for a second group of electronic components 517. These additional contacts or components may be used redundantly with or in addition to the first group of electronic components 502.

Figure 6:
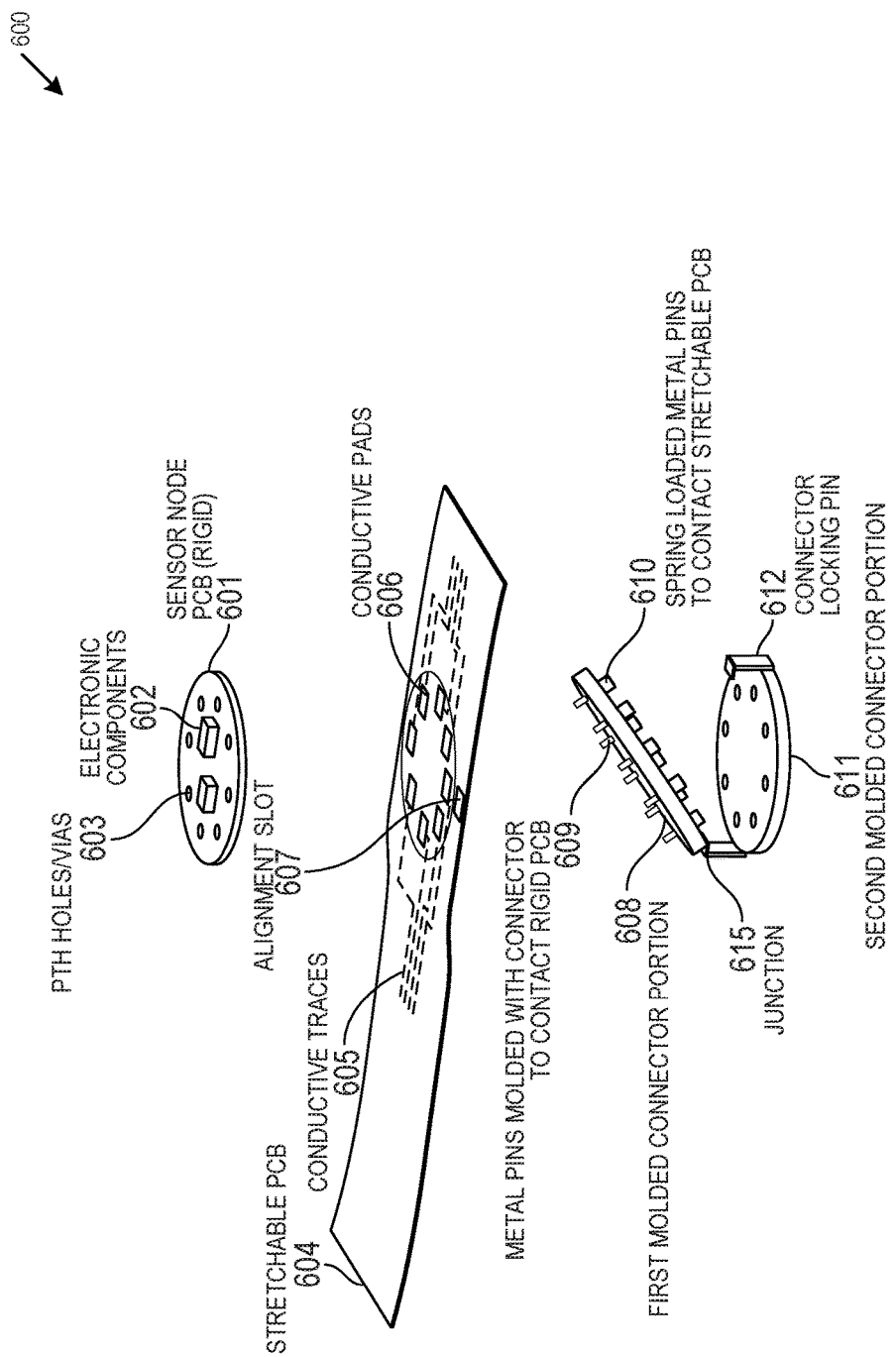
FIG. 6 is a perspective diagram of a sixth stretchable circuit assembly, in accordance with at least one embodiment of the invention.

FIG. 6 is a perspective diagram of a sixth stretchable circuit assembly 600, in accordance with at least one embodiment of the invention. Assembly 600 includes a stretchable PCB 604, where stretchable PCB 604 includes conductive traces 605 and conductive pads 606 fabricated on a flexible or stretchable substrate, such as polyamide polyimide, elastomer material, Thermoplastic Urethane (TPU), fabric, silicone, rubber, or other flexible or stretchable substrate. Assembly 600 includes a rigid sensor node PCB 601, where rigid PCB 601 includes plated-through-hole (PTH) mounting holes 603. First molded connector portion 608 includes multiple pins molded within the plastic base. To provide electrical contacts, the rigid sensor node PCB 601 is placed on metal pins 609 so that the solderable portions of the pins pass through the PTH holes 603. The metal pins 609 are then soldered to the PTH holes 603 to create a single assembly. The spring-loaded metal pins 610 make contact with corresponding conductive pads 606 on the stretchable PCB 604.

Assembly 600 includes a first molded connector portion 608 and a second molded connector portion 611, joined by a hinge junction 615. The combination of the junction 615 and connector locking pin 612 improves the ability of assembly 600 to apply pressure between the metal pins 610 and the conductive pads 606. Junction 615 and connector locking pin 612 provide a hinged, clamshell (e.g., jaw-like) form factor. The clamshell form factor provides easier insertion and removal of the stretchable PCB 604. This clamshell form factor also improves polarity and alignment between the spring-loaded metal pins 610 and the corresponding conductive pads 606. To provide proper alignment of spring-loaded metal pins 610 with corresponding conductive pads 606, the stretchable PCB 604 includes an alignment slot 607. By placing the stretchable PCB 604 on the second molded connector portion 611 such that the connector locking pin 612 is aligned with the alignment slot 607, the conductive pads 606 are aligned with corresponding metal pins 610. Once properly aligned, the locking pin 612 passes through the alignment slot 607 and snap-fits with the first molded connector portion 608. In addition to the mechanical connection provided by junction 615, one or more electrical signals may be routed between the first molded connector portion 608 and the second molded connector portion 611.

Figure 7:
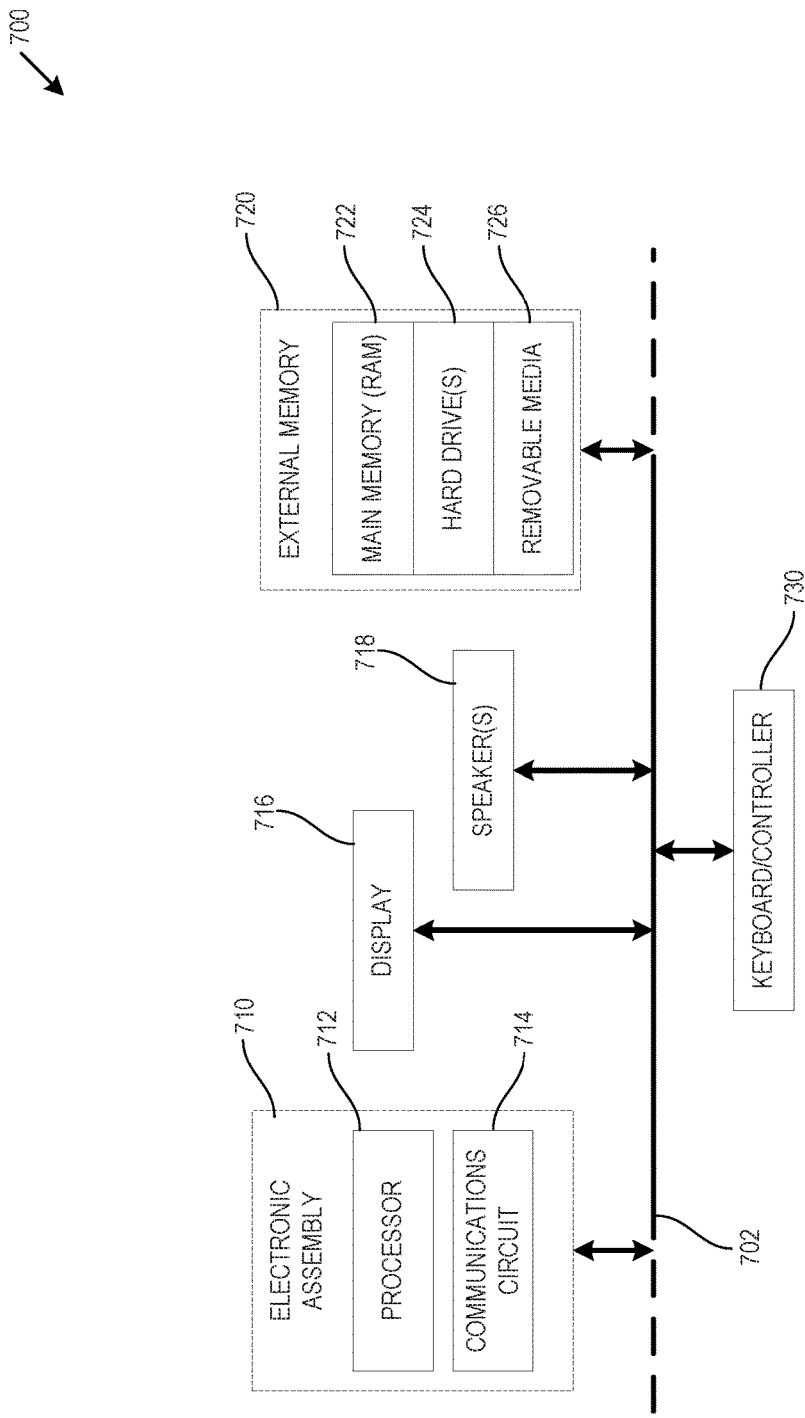
FIG. 7 is a block diagram of an electronic device that may use a circuit interconnect apparatus or method in accordance with at least one embodiment of the invention.

FIG. 7 is a block diagram of a wearable electronic device 700 that may use a circuit interconnect apparatus or method in accordance with at least one embodiment of the invention. FIG. 7 is included to show an example of a higher-level device application for the present invention. In this example, the wearable electronic device 700 comprises a data processing system that includes a system bus 702 to couple the various components of the system. System bus 702 may be implemented within a stretchable PCB, such as through a conductive bus trace within a stretchable PCB or within a rigid PCB conductively connected to a stretchable PCB. System bus 702 provides communications links among the various components of the wearable electronic device 700 and can be implemented as a single bus, as a combination of busses, or in any other suitable manner.

An electronic assembly 710 is coupled to system bus 702, such as through one or more spring-loaded conductive pins connected to a stretchable PCB. The electronic assembly 710 can include any circuit or combination of circuits. In one embodiment, the electronic assembly 710 includes a processor 712 that can be of any type. As used herein, "processor" means any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, or any other type of processor or processing circuit.

Other types of circuits that can be included in electronic assembly 710 are a custom circuit, an application-specific integrated circuit (ASIC) such as one or more circuits (such as a communications circuit 714) for use in wireless devices like mobile telephones, personal data assistants, portable computers, two-way radios, and similar electronic systems. The IC can perform any other type of function.

The wearable electronic device 700 can also include an external memory 720, which in turn can include one or more memory elements suitable to the particular application, such as a main memory 722 in the form of random access memory (RAM), one or more hard drives 724, or one or more drives that handle removable media 726 such as micro SD cards or other removable memory.

The wearable electronic device 700 can also include various wearable input or output devices. For example, wearable electronic device 700 can include a display device 716, one or more speakers 718, and a controller 730, where the control can include a touch screen, voice-recognition device, or any other device that permits a system user to input information into and receive information from the wearable electronic device 700.

To better illustrate the method and apparatuses disclosed herein, a non-limiting list of embodiments is provided here:

Example 1 is an apparatus comprising: a stretchable substrate; a first plurality of substrate contacts disposed on a first side of the stretchable substrate; and a biometric sensor disposed on the stretchable substrate and electrically connected to at least one of the first plurality of substrate contacts.

In Example 2, the subject matter of Example 1 optionally includes a first plurality of contact traces in electrical contact with the first plurality of substrate contacts.

In Example 3, the subject matter of any one or more of Examples 1-2 optionally include a first molded connector portion disposed on the first side of the stretchable substrate, the first molded connector portion including a first plurality of contact pins in electrical contact with the first plurality of substrate contacts.

In Example 4, the subject matter of Example 3 optionally includes wherein each of the first plurality of contact pins includes a first spring-loaded conductive portion to increase the electrical conductivity between the first plurality of contact pins and the first plurality of substrate contacts.

In Example 5, the subject matter of any one or more of Examples 3-4 optionally include a first rigid PCB disposed on and electrically connected to the first molded connector portion.

In Example 6, the subject matter of Example 5 optionally includes the first rigid PCB including a first plurality of plated-through-holes (PTHs), wherein at least a portion of the first plurality of contact pins is disposed inside and electrically connected to the first plurality of PTHs.

In Example 7, the subject matter of any one or more of Examples 5-6 optionally include wherein the first plurality of contact pins are soldered to the first plurality of PTHs to provide an electromechanical connection between the first plurality of contact pins and the first plurality of PTHs.

In Example 8, the subject matter of any one or more of Examples 5-7 optionally include a first plurality of electronic components disposed on and electrically connected to the first rigid PCB.

In Example 9, the subject matter of any one or more of Examples 5-8 optionally include a second molded connector portion disposed on a second side of the stretchable substrate and mechanically connected to the first molded connector portion.

In Example 10, the subject matter of Example 9 optionally includes wherein the second molded connector portion exerts pressure on the stretchable substrate to increase the electrical conductivity between the first plurality of contact pins and the first plurality of substrate contacts.

In Example 11, the subject matter of any one or more of Examples 9-10 optionally include a compressive insert disposed between the second molded connector portion and the stretchable substrate, the compressive insert to exert pressure on the stretchable substrate to increase the electrical conductivity between the first plurality of contact pins and the first plurality of substrate contacts.

In Example 12, the subject matter of any one or more of Examples 9-11 optionally include a second plurality of substrate contacts disposed on a second side of the stretchable substrate.

In Example 13, the subject matter of Example 12 optionally includes wherein the second molded connector portion includes a second plurality of contact pins in electrical contact with the second plurality of substrate contacts.

In Example 14, the subject matter of Example 13 optionally includes wherein each of the second plurality of contact pins includes a second spring-loaded conductive portion to increase the electrical conductivity between the second plurality of contact pins and the second plurality of substrate contacts.

In Example 15, the subject matter of any one or more of Examples 12-14 optionally include a second rigid PCB disposed on and electrically connected to the second molded connector portion.

In Example 16, the subject matter of Example 15 optionally includes the second rigid PCB including a second plurality of PTHs, wherein at least a portion of the second plurality of contact pins is disposed inside and electrically connected to the second plurality of PTHs.

In Example 17, the subject matter of Example 16 optionally includes wherein the second plurality of contact pins are soldered to the second plurality of PTHs to provide an electromechanical connection between the second plurality of contact pins and the second plurality of PTHs.

In Example 18, the subject matter of any one or more of Examples 15-17 optionally include a first plurality of electronic components disposed on and electrically connected to the second rigid PCB.

In Example 19, the subject matter of any one or more of Examples 9-18 optionally include a connector locking pin to provide a detachable mechanical connection between the second molded connector portion and the first molded connector portion.

In Example 20, the subject matter of Example 19 optionally includes a hinged junction between the second molded connector portion and the first molded connector portion, the hinged junction to facilitate separating the second molded connector portion from the first molded connector portion to facilitate installation or removal of the stretchable substrate.

Example 21 is a method comprising: disposing a first plurality of substrate contacts on a first side of a stretchable substrate; disposing a biometric sensor on the stretchable substrate; and electrically connecting the biometric sensor to at least one of the first plurality of substrate contacts.

In Example 22, the subject matter of Example 21 optionally includes wherein electrically connecting the biometric sensor includes electrically connecting the biometric sensor to at least one of a first plurality of contact traces, the first plurality of contact traces in electrical contact with the first plurality of substrate contacts.

In Example 23, the subject matter of any one or more of Examples 21-22 optionally include disposing a first molded connector portion on the first side of the stretchable substrate such that a first plurality of contact pins within the first molded connector portion are in electrical contact with the first plurality of substrate contacts.

In Example 24, the subject matter of Example 23 optionally includes wherein each of the first plurality of contact pins includes a first spring-loaded conductive portion to increase the electrical conductivity between the first plurality of contact pins and the first plurality of substrate contacts.

In Example 25, the subject matter of any one or more of Examples 23-24 optionally include disposing a first rigid PCB on the first molded connector portion.

In Example 26, the subject matter of Example 25 optionally includes disposing at least a portion of the first plurality of contact pins inside a first plurality of plated-through-holes (PTHs) within the first rigid PCB.

In Example 27, the subject matter of any one or more of Examples 25-26 optionally include soldering the first plurality of contact pins to the first plurality of PTHs to provide an electromechanical connection between the first plurality of contact pins and the first plurality of PTHs.

In Example 28, the subject matter of any one or more of Examples 25-27 optionally include disposing a first plurality of electronic components on the first rigid PCB.

In Example 29, the subject matter of any one or more of Examples 25-28 optionally include disposing a second molded connector portion a second side of the stretchable substrate; and mechanically connecting the second molded connector portion to the first molded connector portion.

In Example 30, the subject matter of Example 29 optionally includes wherein the second molded connector portion exerts pressure on the stretchable substrate to increase the electrical conductivity between the first plurality of contact pins and the first plurality of substrate contacts.

In Example 31, the subject matter of any one or more of Examples 29-30 optionally include disposing a compressive insert between the second molded connector portion and the stretchable substrate, the compressive insert to exert pressure on the stretchable substrate to increase the electrical conductivity between the first plurality of contact pins and the first plurality of substrate contacts.

In Example 32, the subject matter of any one or more of Examples 29-31 optionally include disposing a second plurality of substrate contacts on a second side of the stretchable substrate.

In Example 33, the subject matter of Example 32 optionally includes disposing a second plurality of contact pins in electrical contact with the second plurality of substrate contacts, wherein the second molded connector portion includes the second plurality of contact pins.

In Example 34, the subject matter of Example 33 optionally includes wherein each of the second plurality of contact pins includes a second spring-loaded conductive portion to increase the electrical conductivity between the second plurality of contact pins and the second plurality of substrate contacts.

In Example 35, the subject matter of any one or more of Examples 32-34 optionally include disposing a second rigid PCB on the second molded connector portion.

In Example 36, the subject matter of Example 35 optionally includes disposing at least a portion of the second plurality of contact pins within a second plurality of PTHs in the second rigid PCB.

In Example 37, the subject matter of Example 36 optionally includes soldering the second plurality of contact pins to the second plurality of PTHs to provide an electromechanical connection between the second plurality of contact pins and the second plurality of PTHs.

In Example 38, the subject matter of any one or more of Examples 35-37 optionally include disposing a first plurality of electronic components on and electrically connected to the second rigid PCB.

In Example 39, the subject matter of any one or more of Examples 29-38 optionally include securing a connector locking pin to provide a detachable mechanical connection between the second molded connector portion and the first molded connector portion.

In Example 40, the subject matter of Example 39 optionally includes detaching the connector locking pin; separating the second molded connector portion from the first molded connector portion; replacing the stretchable substrate with a replacement stretchable substrate; securing the second molded connector portion to the first molded connector portion; and reattaching the connector locking pin.

In Example 41, the subject matter of Example 40 optionally includes wherein separating the second molded connector portion from the first molded connector portion includes opening a hinged junction between the second molded connector portion and the first molded connector portion, the hinged junction to facilitate installation or removal of the stretchable substrate.

Example 42 is a machine-readable medium including instructions, which when executed by a computing system, cause the computing system to perform any of the methods of Examples 21-41.

Example 43 is an apparatus comprising means for performing any of the methods of Examples 21-41.

Example 44 is at least one machine-readable storage medium, comprising a plurality of instructions that, responsive to being executed with processor circuitry of a computer-controlled device, cause the computer-controlled device to: dispose a first plurality of substrate contacts on a first side of a stretchable substrate; dispose a biometric sensor on the stretchable substrate; and electrically connect the biometric sensor to at least one of the first plurality of substrate contacts.

In Example 45, the subject matter of Example 44 optionally includes the instructions further causing the computer-controlled device to electrically connect the biometric sensor to at least one of a first plurality of contact traces, the first plurality of contact traces in electrical contact with the first plurality of substrate contacts.

In Example 46, the subject matter of any one or more of Examples 44-45 optionally include the instructions further causing the computer-controlled device to dispose a first molded connector portion on the first side of the stretchable substrate such that a first plurality of contact pins within the first molded connector portion are in electrical contact with the first plurality of substrate contacts.

In Example 47, the subject matter of Example 46 optionally includes wherein each of the first plurality of contact pins includes a first spring-loaded conductive portion to increase the electrical conductivity between the first plurality of contact pins and the first plurality of substrate contacts.

In Example 48, the subject matter of any one or more of Examples 46-47 optionally include the instructions further causing the computer-controlled device to dispose a first rigid PCB on the first molded connector portion.

In Example 49, the subject matter of Example 48 optionally includes the instructions further causing the computer-controlled device to dispose at least a portion of the first plurality of contact pins inside a first plurality of plated-through-holes (PTHs) within the first rigid PCB.

In Example 50, the subject matter of any one or more of Examples 48-49 optionally include the instructions further causing the computer-controlled device to solder the first plurality of contact pins to the first plurality of PTHs to provide an electromechanical connection between the first plurality of contact pins and the first plurality of PTHs.

In Example 51, the subject matter of any one or more of Examples 48-50 optionally include the instructions further causing the computer-controlled device to dispose a first plurality of electronic components on the first rigid PCB.

In Example 52, the subject matter of any one or more of Examples 48-51 optionally include the instructions further causing the computer-controlled device to: dispose a second molded connector portion a second side of the stretchable substrate; and mechanically connect the second molded connector portion to the first molded connector portion.

In Example 53, the subject matter of Example 52 optionally includes wherein the second molded connector portion exerts pressure on the stretchable substrate to increase the electrical conductivity between the first plurality of contact pins and the first plurality of substrate contacts.

In Example 54, the subject matter of any one or more of Examples 52-53 optionally include the instructions further causing the computer-controlled device to dispose a compressive insert between the second molded connector portion and the stretchable substrate, the compressive insert to exert pressure on the stretchable substrate to increase the electrical conductivity between the first plurality of contact pins and the first plurality of substrate contacts.

In Example 55, the subject matter of any one or more of Examples 52-54 optionally include the instructions further causing the computer-controlled device to dispose a second plurality of substrate contacts on a second side of the stretchable substrate.

In Example 56, the subject matter of Example 55 optionally includes the instructions further causing the computer-controlled device to dispose a second plurality of contact pins in electrical contact with the second plurality of substrate contacts, wherein the second molded connector portion includes the second plurality of contact pins.

In Example 57, the subject matter of Example 56 optionally includes wherein each of the second plurality of contact pins includes a second spring-loaded conductive portion to increase the electrical conductivity between the second plurality of contact pins and the second plurality of substrate contacts.

In Example 58, the subject matter of any one or more of Examples 55-57 optionally include the instructions further causing the computer-controlled device to dispose a second rigid PCB on the second molded connector portion.

In Example 59, the subject matter of Example 58 optionally includes the instructions further causing the computer-controlled device to dispose at least a portion of the second plurality of contact pins within a second plurality of PTHs in the second rigid PCB.

In Example 60, the subject matter of Example 59 optionally includes the instructions further causing the computer-controlled device to solder the second plurality of contact pins to the second plurality of PTHs to provide an electromechanical connection between the second plurality of contact pins and the second plurality of PTHs.

In Example 61, the subject matter of any one or more of Examples 58-60 optionally include the instructions further causing the computer-controlled device to dispose a first plurality of electronic components on and electrically connected to the second rigid PCB.

In Example 62, the subject matter of any one or more of Examples 52-61 optionally include the instructions further causing the computer-controlled device to secure a connector locking pin to provide a detachable mechanical connection between the second molded connector portion and the first molded connector portion.

In Example 63, the subject matter of Example 62 optionally includes the instructions further causing the computer-controlled device to: detach the connector locking pin; separate the second molded connector portion from the first molded connector portion; replace the stretchable substrate with a replacement stretchable substrate; secure the second molded connector portion to the first molded connector portion; and reattach the connector locking pin.

In Example 64, the subject matter of Example 63 optionally includes the instructions further causing the computer-controlled device to open a hinged junction between the second molded connector portion and the first molded connector portion, the hinged junction to facilitate installation or removal of the stretchable substrate.

Example 65 is an apparatus comprising: means for disposing a first plurality of substrate contacts on a first side of a stretchable substrate; means for disposing a biometric sensor on the stretchable substrate; and means for electrically connecting the biometric sensor to at least one of the first plurality of substrate contacts.

In Example 66, the subject matter of Example 65 optionally includes wherein means for electrically connecting the biometric sensor includes means for electrically connecting the biometric sensor to at least one of a first plurality of contact traces, the first plurality of contact traces in electrical contact with the first plurality of substrate contacts.

In Example 67, the subject matter of any one or more of Examples 65-66 optionally include means for disposing a first molded connector portion on the first side of the stretchable substrate such that a first plurality of contact pins within the first molded connector portion are in electrical contact with the first plurality of substrate contacts.

In Example 68, the subject matter of Example 67 optionally includes wherein each of the first plurality of contact pins includes a first spring-loaded conductive portion to increase the electrical conductivity between the first plurality of contact pins and the first plurality of substrate contacts.

In Example 69, the subject matter of any one or more of Examples 67-68 optionally include means for disposing a first rigid PCB on the first molded connector portion.

In Example 70, the subject matter of Example 69 optionally includes means for disposing at least a portion of the first plurality of contact pins inside a first plurality of plated-through-holes (PTHs) within the first rigid PCB.

In Example 71, the subject matter of any one or more of Examples 69-70 optionally include means for soldering the first plurality of contact pins to the first plurality of PTHs to provide an electromechanical connection between the first plurality of contact pins and the first plurality of PTHs.

In Example 72, the subject matter of any one or more of Examples 69-71 optionally include means for disposing a first plurality of electronic components on the first rigid PCB.

In Example 73, the subject matter of any one or more of Examples 69-72 optionally include means for disposing a second molded connector portion a second side of the stretchable substrate; and means for mechanically connecting the second molded connector portion to the first molded connector portion.

In Example 74, the subject matter of Example 73 optionally includes wherein the second molded connector portion exerts pressure on the stretchable substrate to increase the electrical conductivity between the first plurality of contact pins and the first plurality of substrate contacts.

In Example 75, the subject matter of any one or more of Examples 73-74 optionally include means for disposing a compressive insert between the second molded connector portion and the stretchable substrate, the compressive insert to exert pressure on the stretchable substrate to increase the electrical conductivity between the first plurality of contact pins and the first plurality of substrate contacts.

In Example 76, the subject matter of any one or more of Examples 73-75 optionally include means for disposing a second plurality of substrate contacts on a second side of the stretchable substrate.

In Example 77, the subject matter of Example 76 optionally includes means for disposing a second plurality of contact pins in electrical contact with the second plurality of substrate contacts, wherein the second molded connector portion includes the second plurality of contact pins.

In Example 78, the subject matter of Example 77 optionally includes wherein each of the second plurality of contact pins includes a second spring-loaded conductive portion to increase the electrical conductivity between the second plurality of contact pins and the second plurality of substrate contacts.

In Example 79, the subject matter of any one or more of Examples 76-78 optionally include means for disposing a second rigid PCB on the second molded connector portion.

In Example 80, the subject matter of Example 79 optionally includes means for disposing at least a portion of the second plurality of contact pins within a second plurality of PTHs in the second rigid PCB.

In Example 81, the subject matter of Example 80 optionally includes means for soldering the second plurality of contact pins to the second plurality of PTHs to provide an electromechanical connection between the second plurality of contact pins and the second plurality of PTHs.

In Example 82, the subject matter of any one or more of Examples 79-81 optionally include means for disposing a first plurality of electronic components on and electrically connected to the second rigid PCB.

In Example 83, the subject matter of any one or more of Examples 73-82 optionally include means for securing a connector locking pin to provide a detachable mechanical connection between the second molded connector portion and the first molded connector portion.

In Example 84, the subject matter of Example 83 optionally includes means for detaching the connector locking pin; means for separating the second molded connector portion from the first molded connector portion; means for replacing the stretchable substrate with a replacement stretchable substrate; means for securing the second molded connector portion to the first molded connector portion; and means for reattaching the connector locking pin.

In Example 85, the subject matter of Example 84 optionally includes wherein means for separating the second molded connector portion from the first molded connector portion includes means for opening a hinged junction between the second molded connector portion and the first molded connector portion, the hinged junction to facilitate installation or removal of the stretchable substrate.

These and other examples and features of the present stretchable substrates, stretchable substrate systems, and related methods will be set forth in part in the following detailed description. This overview is intended to provide non-limiting examples of the present subject matter—it is not intended to provide an exclusive or exhaustive explanation. The detailed description below is included to provide further information about the present stretchable substrates, stretchable substrate systems, and methods.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An apparatus comprising:
    a stretchable substrate;
    a first plurality of substrate contacts disposed on a first side of the stretchable substrate;
    a biometric sensor disposed on the stretchable substrate and electrically connected to at least one of the first plurality of substrate contacts;
    a first molded connector portion disposed on the first side of the stretchable substrate, the first molded connector portion including a first plurality of contact pins in electrical contact with the first plurality of substrate contacts; and
    a second molded connector portion disposed on a second side of the stretchable substrate and mechanically connected to the first molded connector portion, the second molded connector portion exerting pressure on the stretchable substrate to increase the electrical conductivity between the first plurality of contact pins and the first plurality of substrate contacts.

2. The apparatus of 1, further including a first plurality of contact traces in electrical contact with the first plurality of substrate contacts.

3. The apparatus of 1, wherein each of the first plurality of contact pins includes a first spring-loaded conductive portion to increase the electrical conductivity between the first plurality of contact pins and the first plurality of substrate contacts.

4. The apparatus of 1, further including a first rigid PCB disposed on and electrically connected to the first molded connector portion.

5. The apparatus of 4, further including a first plurality of electronic components disposed on and electrically connected to the first rigid PCB.

6. The apparatus of 1, further including a compressive insert disposed between the second molded connector portion and the stretchable substrate, the compressive insert to exert pressure on the stretchable substrate to increase the electrical conductivity between the first plurality of contact pins and the first plurality of substrate contacts.

7. The apparatus of 1, further including a connector locking pin to provide a detachable mechanical connection between the second molded connector portion and the first molded connector portion.

8. The apparatus of 1, further including a hinged junction between the second molded connector portion and the first molded connector portion, the hinged junction to facilitate separating the second molded connector portion from the first molded connector portion to facilitate installation or removal of the stretchable substrate.

9. A method comprising:
    disposing a first plurality of substrate contacts on a first side of a stretchable substrate;
    disposing a biometric sensor on the stretchable substrate;
    electrically connecting the biometric sensor to at least one of the first plurality of substrate contacts;
    disposing a first molded connector portion on the first side of the stretchable substrate such that a first plurality of contact pins within the first molded connector portion are in electrical contact with the first plurality of substrate contacts;
    disposing a second molded connector portion a second side of the stretchable substrate; and
    mechanically connecting the second molded connector portion to the first molded connector portion, the second molded connector portion exerting pressure on the stretchable substrate to increase an electrical conductivity between the first plurality of contact pins and the first plurality of substrate contacts.

10. The method of 9, further including disposing a first rigid PCB on the first molded connector portion.

11. At least one machine-readable storage medium, comprising a plurality of instructions that, responsive to being executed with processor circuitry of a computer-controlled device, cause the computer-controlled device to:
    dispose a first plurality of substrate contacts on a first side of a stretchable substrate;
    dispose a biometric sensor on the stretchable substrate;
    electrically connect the biometric sensor to at least one of the first plurality of substrate contacts
    dispose a first molded connector portion on the first side of the stretchable substrate such that a first plurality of contact pins within the first molded connector portion are in electrical contact with the first plurality of substrate contacts;
    dispose a second molded connector portion a second side of the stretchable substrate; and
    mechanically connect the second molded connector portion to the first molded connector portion, the second molded connector portion exerting pressure on the stretchable substrate to increase an electrical conductivity between the first plurality of contact pins and the first plurality of substrate contacts.

12. The at least one machine-readable storage medium of 11, the instructions further causing the computer-controlled device to electrically connect the biometric sensor to at least one of a first plurality of contact traces, the first plurality of contact traces in electrical contact with the first plurality of substrate contacts.

13. The at least one machine-readable storage medium of 11, the instructions further causing the computer-controlled device to dispose a first rigid PCB on the first molded connector portion.

14. The method of 9, further including disposing a first molded connector portion on the first side of the stretchable substrate such that a first plurality of contact pins within the first molded connector portion are in electrical contact with the first plurality of substrate contacts, wherein each of the first plurality of contact pins includes a first spring-loaded conductive portion to increase the electrical conductivity between the first plurality of contact pins and the first plurality of substrate contacts.

15. The method of 9, further including disposing a compressive insert between the second molded connector portion and the stretchable substrate, the compressive insert to exert pressure on the stretchable substrate to increase the electrical conductivity between the first plurality of contact pins and the first plurality of substrate contacts.

16. The method of 9, further including securing a connector locking pin to provide a detachable mechanical connection between the second molded connector portion and the first molded connector portion.

17. The at least one machine-readable storage medium of 11, the instructions further causing the computer-controlled device to dispose a first molded connector portion on the first side of the stretchable substrate such that a first plurality of contact pins within the first molded connector portion are in electrical contact with the first plurality of substrate contacts, wherein each of the first plurality of contact pins includes a first spring-loaded conductive portion to increase the electrical conductivity between the first plurality of contact pins and the first plurality of substrate contacts.

18. The at least one machine-readable storage medium of 11, the instructions further causing the computer-controlled device to dispose a compressive insert between the second molded connector portion and the stretchable substrate, the compressive insert to exert pressure on the stretchable substrate to increase the electrical conductivity between the first plurality of contact pins and the first plurality of substrate contacts.

19. The at least one machine-readable storage medium of 11, the instructions further causing the computer-controlled device to secure a connector locking pin to provide a detachable mechanical connection between the second molded connector portion and the first molded connector portion.

* * * * *